United States Patent [19]

Miyasaka et al.

[11] Patent Number: 4,899,903
[45] Date of Patent: Feb. 13, 1990

[54] TUBE ASSEMBLY PROVIDED WITH A BREAKAWAY PLUG

[75] Inventors: Eiichi Miyasaka; Tetsuro Nishimura; Nobukazu Tanokura, all of Shizuoka, Japan

[73] Assignee: Terumo Kabushiki Kaisha, Tokyo, Japan

[21] Appl. No.: 212,185

[22] Filed: Jun. 27, 1988

[51] Int. Cl.$^4$ .............................................. B65D 41/32
[52] U.S. Cl. ....................................... 220/266; 138/89; 604/111; 604/244
[58] Field of Search ............... 215/253, 256; 220/276, 220/266; 604/244, 111; 138/89

[56] References Cited

U.S. PATENT DOCUMENTS 3,994,412  11/1976  Difiglio ............................... 220/266
4,415,393  11/1983  Grimes ............................. 220/276 X
4,632,267  12/1986  Fowles et al. .................... 220/266 X Primary Examiner—Donald F. Norton
Attorney, Agent, or Firm—Burns, Doane, Swecker & Mathis

[57] ABSTRACT

An assembly of a tube having a breakaway plug member mounted on one opening thereof is provided. The plug member has an open end and a closed end, and includes on its inner surface a first inner-wall portion extending from the open end toward the closed end a predetermined distance which is fixedly secured to the one open end of said tubular body, and a second inner-wall portion defining a space therein which extends from the first inner-wall portion to the closed end. The plug member also includes on its outer surface a thin-walled frangible portion located on or radially outside the second inner-wall portion which is breakable to allow separation of the plug member from the tubular body. The one open end of the tubular body extends in said space beyond the thin-walled frangible portion toward the closed end of the plug member.

3 Claims, 6 Drawing Sheets

FIG. 5a
(PRIOR ART)
FIG. 5b
(PRIOR ART)
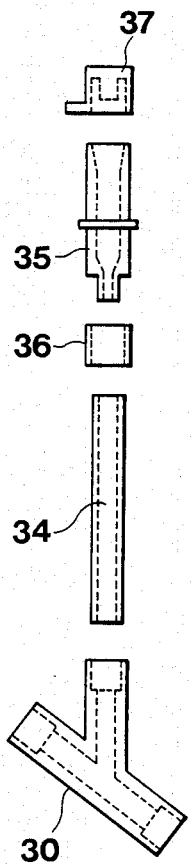
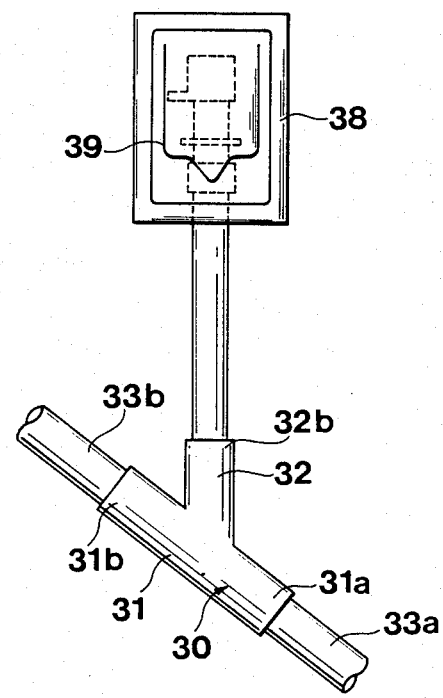

TUBE ASSEMBLY PROVIDED WITH A BREAKAWAY PLUG

BACKGROUND OF THE INVENTION

1. Field of the Invention

This invention relates to a medical tube assembly. More particularly, it relates to a tube assembly provided with a breakaway plug which is very unlikely to be contaminated during connection with another member.

2. Description of Related Art

Referring to FIG. 5b, there is illustrated one prior art tube assembly. A Y-shaped branch tube 30 illustrated in FIG. 5b comprises a main tube 31 and a branch tube 32. The main tube 31 has two openings, that is, a proximal opening 31a to be connected to a venipuncture needle (not shown) for blood collection, and a distal opening 31b to be connected to a tubing 33b which is further connected to a blood bag (not shown). The branch tube 32 has a distal opening 32b which has a blood-returning assembly mounted thereon.

The component constituting the blood-returning assembly are shown together with the branch tube 30 in FIG. 5a in an exploded state. The blood returning assembly comprises a sleeve 34 mounted on the distal opening 32b, connector 35 fitted in the sleeve 34, caulking member 36 to fluid-tightly join the sleeve 34 and the connector 35, and a rubber cap 37 fitted on the connector 35. The blood returning assembly is enclosed in an envelope 38 for preventing contamination. The envelope 38 has a peeling line 39 for ease of opening the envelope 38.

Upon returning blood corpuscles, the envelope 38 is opened at the peeling line 39, and the cap 37 is then removed for connecting another member to the connector 35.

The blood returning assembly as described above has a plurality of drawbacks as described below.

(1) Since the blood returning assembly comprises a number of components, the number of joints are also increased resulting in an increased risk of contamination. Efficiency in course of assembly is also lowered.

(2) Since the medical solution in the blood bag directly contacts the rubber cap via tubings, amount of the substances eluted from the rubber cap is increased although the amount is below the standard value.

(3) The rubber cap may be loosened, or even come off in an extreme case, due to an increased inner pressure of the blood bag during an autoclave sterilization of the system.

(4) The blood returning assembly is wrapped with the envelope by way of precaution against the contamination in (3). Upon returning the blood corpuscles, a troublesome step of opening the envelope is required before taking the rubber cap off. Complicated operation increases the risk of contamination and lowers the operation efficiency.

SUMMARY OF THE INVENTION

An object of the present invention is to provide a tube assembly having a breakaway plug which has eliminated the above-described drawbacks of the prior art plug.

Another object of the present invention is to provide a tube assembly having a breakaway plug wherein an easy insertion into the torn end of the tube of another member such as a spiked end of a tubing is enabled to perfectly eliminate risk of contamination upon connection.

According to the present invention, there is provided a tube assembly with a breakaway plug comprising
 a tubular body having at least two open ends; and
 a plug member having an open end and a closed end mounted on one open end of said tubular body,
  said plug member including on its inner surface
   a first inner-wall portion extending from the open end toward the closed end a predetermined distance which is fixedly secured to the one open end of said tubular body, and
   a second inner-wall portion extending from the first inner-wall portion to the closed end to define a space therein, and
  said plug member including on its outer surface
   a thin-walled frangible portion located on or radially outside said second inner-wall portion which is breakable to allow separation of said plug member from said tubular body, and
   said one open end of the tubular body extending in said space beyond the thin-walled frangible portion toward the closed end of the plug member.

According to one embodiment of the present invention, there is provided the tube assembly wherein said second inner-wall portion has a relatively larger inner diameter than the first inner-wall portion.

According to another embodiment of the present invention, there is provided the tube assembly wherein said one open end of the tubular body includes on its outer surface a first outer-wall portion on which the first inner-wall portion of the plug member is fixedly secured, and a second outer-wall portion defining the space between the second inner-wall portion of the plug member, said second outer-wall portion having a relatively smaller outer diameter than said first-outer wall portion.

BRIEF DESCRIPTION OF THE DRAWINGS

The above and other objects, features, and advantages of the present invention will be more fully understood by reading the following description when taken in conjunction with the accompanying drawings, in which:

FIG. 5a is an exploded view of a prior art tube assembly;

FIG. 5b is a front view of the prior art tube assembly in an assembled state.

DETAILED DESCRIPTION OF THE PREFERRED EMBODIMENT

The tube assembly of the present invention includes a tube body having at least two open ends. Any tubular body having at least two open ends between which a flow path extends may be employed. Although a commonly used four-way branch tube is referred to as a typical example in the following description, the present invention is not limited to the four-way branch tube.

Figure 1:
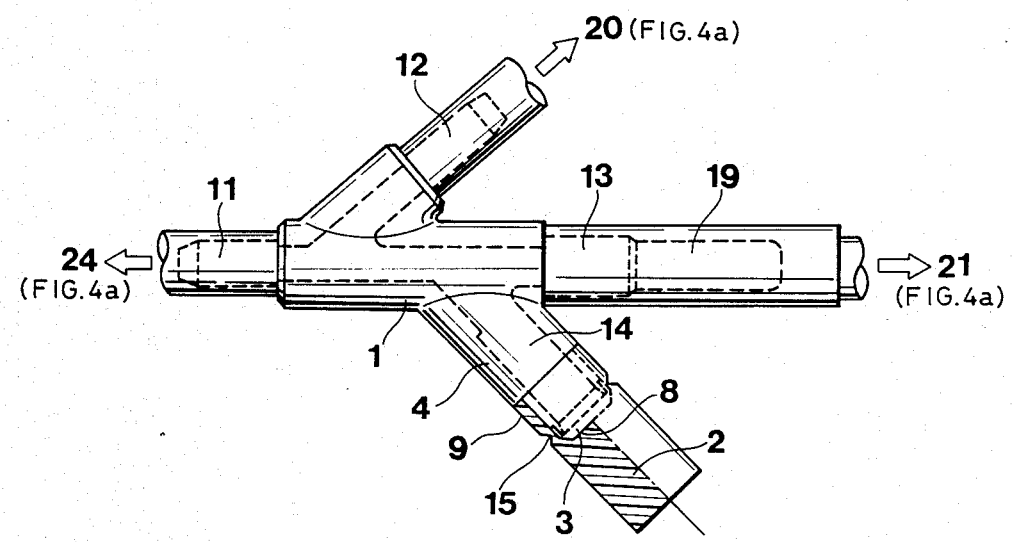
FIG. 1 illustrates a tube assembly with a breakaway plug according to one embodiment of the present invention.

Referring to FIG. 1, there is illustrated a four-way branch tube according to one embodiment of the present invention. It will be understood that FIG. 1 is an enlarged view corresponding to a circled portion in the system of FIG. 4a.

Figure 4A:
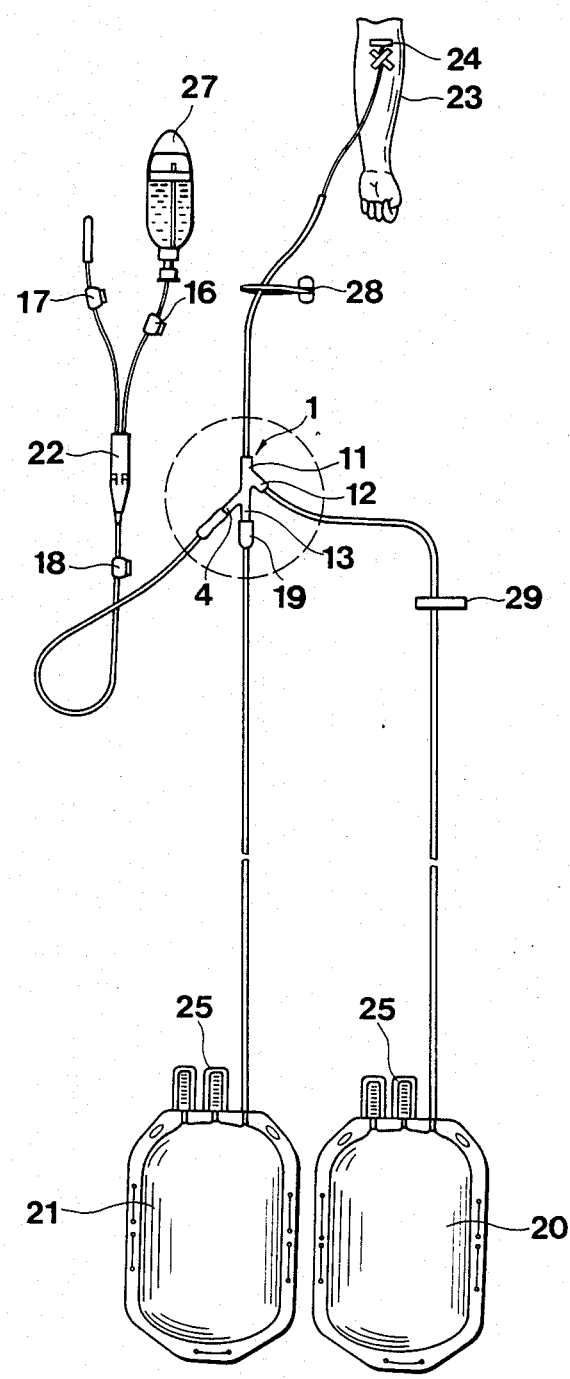
FIGS. 4a and 4b are schematic views of a plasmapheresis system having the tube assembly of the invention incorporated therein.

The four-way branch tube illustrated in FIG. 1 has four openings, that is, a first opening 11 to be connected to a venipuncture needle 24 for blood collection, a second opening 12 to be connected to a first blood bag 20, a third opening 13 to be connected to a second blood bag 21, and a fourth opening 14 having a plug member 2 mounted thereon (see FIG. 4a).

For brevity of description, a flow path communicating between the first and second openings 11 and 13 is designated a main flow path. With respect to the main flow path, the first opening 11 to be connected to the needle 24 is designated a proximal end and the second, third and fourth openings 12, 13 and 14 are designated distal ends.

The feature of the present invention resides in a combination of the branch 4 and a plug member 2. The components according to one embodiment of the present invention are described in detail in FIG. 2a, which is a cross-sectional view of the branch 4 and the plug member 2 in an exploded state. A full assembly of these components is shown in FIG. 2b.

The branch 4 of the four-way branch tube 1 has a flow path-defining bore 14 terminating at an open end 6 and includes a stepped wall portion having a smaller outside diameter than the remaining part of the branch 4. The outside wall of the branch is stepped to form the smaller outside diameter wall portion 5 for mounting the plug member 2 thereon.

The plug member 2 has an open end 7 and a closed end 8, and on its inner surface a first inner-wall portion 9 and a second inner-wall portion 10. The first inner-wall portion 9 extends from the open end 7 toward the closed end 8 a predetermined distance, and is fixedly secured to the stepped wall portion 5 of the branch 4 as shown in FIG. 2b. The second inner-wall portion 10 extends from the first inner-wall portion 9 to the closed end 8 to define a space 3 therein. In this embodiment, the second inner-wall portion 10 has a larger inner diameter than the first inner-wall portion 9. The plug member 2 includes on its outer surface a thin-walled portion or a circumferential notch 15 located radially outside the second inner-wall portion 10 of relatively larger diameters for allowing at least a portion of the plug member 2 to be separated from the tubular body 1. However, the thin-walled portion may be provided on the second inner-wall portion 10.

Figure 2A:
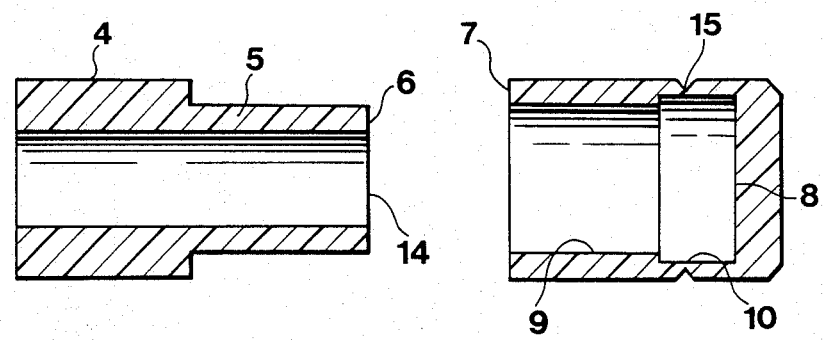
FIG. 2a is an exploded cross-sectional view of the tube assembly showing a tube and a plug in a disassembled state.
Figure 2B:
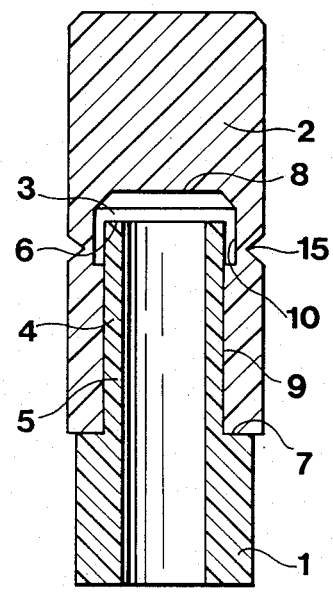
FIG. 2b is a cross-sectional view of the tube assembly showing the tube and the plug member in an assembled state.

FIG. 2b shows the components in an assembled state. The plug member 2 is mounted on the branch 4 to close its opening 14. The first inner-wall portion 9 of the plug member 2 is in snug fit over the stepped wall portion 5 of the branch 4. A space 3 is left between the second inner-portion 10 of the plug member 2 and the stepped wall portion 5 of the branch 4 in radial direction. The space 3 is sufficient to keep the open end 6 of the branch 4 from obstructing in breaking the plug member 2 at its thin-walled frangible portion 15. For the same reason, the distal or open end 6 of the branch 4 is axially spaced apart from the closed end 8 of the plug member 2.

Figure 3:
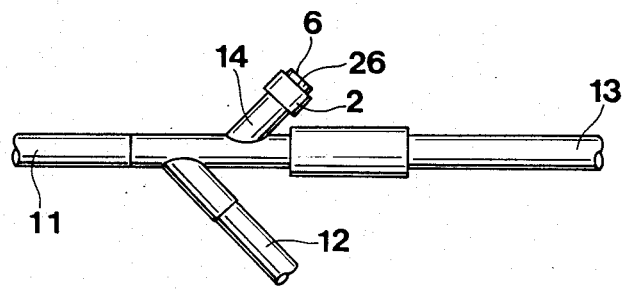
FIG. 3 is a front view of the tube assembly of the present invention after breaking the plug member.

In the present invention, it is important that the open end 6 of the branch 4 axially extends beyond the thin-walled portion 15 of the plug member 2 toward the closed end 8 of the plug member 2. After the plug member 2 is removed by tearing off the plug member 2 at the thin-walled portion 15, the open end 6 of the branch 4 protrudes beyond a cut edge 26 of the remainder of the plug member 2 left attached to the branch 4, as shown in FIG. 3. When it is desired to connect another connecting member, for example, a spiked end of a tubing, to the open end 6 of the branch 4, the open end 6 is exposed beyond the cut edge 26 of the plug residue and thus clearly visible to ensure safe connection. There is little likelihood that the other connecting member be inadvertently contacted to the cut edge 26 of the plug member 2 which would be sometimes contaminated, thus avoiding contamination of the flow path.

Location of the thin-walled portion 15 in the outside wall of the second inner-wall portion 10 means that the thin-walled portion 15 is located radially outside the space 3 between the plug member 2 and the branch 4. Then it is very easy to tear off the plug 2 as by twisting or bending even when the plug is made of a relatively flexible material.

Figure 6:
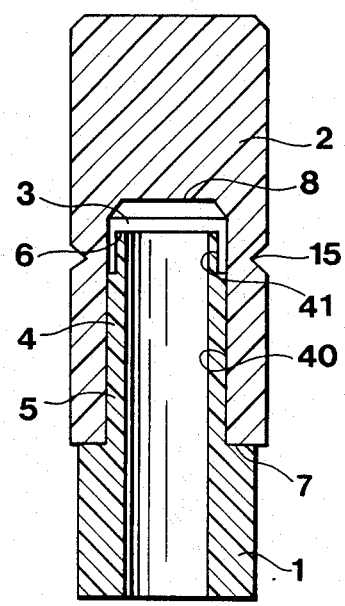
FIG. 6 is the tube assembly with a breakaway plug according to another embodiment of the present invention.

Although the tube assembly of the present invention has been set forth in accordance with the embodiment illustrated in FIGS. 2a and 2b, another embodiment as shown in FIG. 6 is also preferable.

In the embodiment of FIGS. 2a and 2b, the second inner-wall portion 10 had a larger inner diameter than the first inner-wall portion 9, and the stepped wall portion 5 had a uniform diameter.

On the other hand, in the embodiment of FIG. 6, the stepped wall portion 5 includes a first outer-wall portion 40 on which the first inner-wall portion 9 of the plug member 2 is fixedly secured, and a second outer-wall portion 41 defining the space 3 between the second inner-wall portion 10 of the plug member 2, and said second outer-wall portion 41 has a smaller outer diameter than the first outer-wall portion 40. The first inner-wall portion 9 and the second inner-wall portion 10 of the plug member has an equivalent diameter. Location of the thin-walled portion 15 in the outside wall of the second inner-wall portion 10 means that the thin-walled portion 15 is located radially outside the space 3 defined between the second outer-wall portion 41 of the branch 4 having a smaller outer diameter and the second inner-wall portion 10 of the plug member 2. Then it is again very easy to tear off the plug member 2 by twisting even when the plug is made of a relatively flexible material.

The branch tube 1 and the plug member 2 may be adhered with an adhesive or a solvent. However, in order to avoid the contamination of the fluid to be passed therethrough, typically blood, it is preferable that the plug member is fixedly secured to the branch tube 1 by means of a blocking bond achieved by the heat applied during autoclave sterilization.

Although the branch tube 1 and the plug member 2 may be fabricated from the same material as flexible blood bags or tubings, it is preferable that they are fabricated from a relatively rigid material. Typical examples of relatively rigid material are rigid polyvinyl chloride, polycarbonate resin, and the like. The most preferable material for the plug member 2 is polycarbonate resin in terms of operativity upon breaking and the smooth cut edge after breaking. The branch tube 1 and the plug 2 may be fabricated from either the same or different material.

Operation

The operation of the four-way branch tube provided with the plug member 2 on one branch as shown in FIG. 1 is described by referring to a system for plasmapheresis therapy having the branch tube 1 incorporated therein.

As shown in FIG. 4a, the plasmapheresis system includes four sections of tubing connected to the four-way branch tube 1. A first section of tubing extends from a venipuncture needle 24 to the first opening 11 of the branch tube 1 for the purpose of blood collection and has a hemostat 28 thereon. A second section of tubing extends from the second opening 12 to a first blood bag 20 and has a hemostat 29 thereon. A third section of tubing extends from the third opening 13 of the branch tube to a second blood bag 21 via the frangible valve 19. A fourth section of tubing extends from the fourth opening 14 to a Y set 22. The fourth section of tubing is a trunk line of the Y set 22 which includes a first inlet line extending to a physiological saline bottle 27 through a clamp 16 and a second inlet line having a clamp 17. This is an outline of the system, and all the lines are not connected at the same time. Connection will become apparent from the following description of operation.

While the roller clamps 16, 17 and 18 associated with the Y set 22 are closed, a spiked end portion of the line with the clamp 16 is pierced into the saline bottle 27. The roller clamp 16 is then opened and the clamp 18 is released to prime the Y set 22, and the roller clamp 18 is again closed.

During this operation, the plug member 2 of the branch tube 1 of the present invention designated by a circle in FIG. 4a is kept unbroken. The frangible valve 19 is also kept unbroken so that the flow path to the second blood bag 21 is closed.

The next step is to connect a connector at the free end of the Y set trunk to the branch 4 of the branch tube 1. Before tearing off the plug member 2 at the thinwalled portion 15, a hemostat 29 is fastened to prevent a reverse flow of medical solution from the first blood bag 20.

The plug member 2 is then broken at the thin-walled portion 15 by bending or twisting, and the end 6 of the branch 4 is now protruding out of the torn end 26 of the plug member 2. The connector of the Y set 22 is connected to the protruding end 6 of the branch 4. Since the end 6 is protruded, connection can be readily effected. The risk of contamination is also minimized since the connector does not contact with any other members.

The next step is to collect blood from the donor 23. The hemostat 28 is placed at a tubing in proximity of the venipuncture needle 24. The venipuncture is made and the hemostat 28 is removed after ascertaining that the blood is flowing into the tubing. The hemostat 29 is also removed to communicate an open continuous flow path to the first blood bag 20. Since the flow path to the second blood bag 21 is closed with the frangible valve 19, the blood flows from the venipuncture needle 24 into the first blood bag 20 by gravity.

Figure 4B:
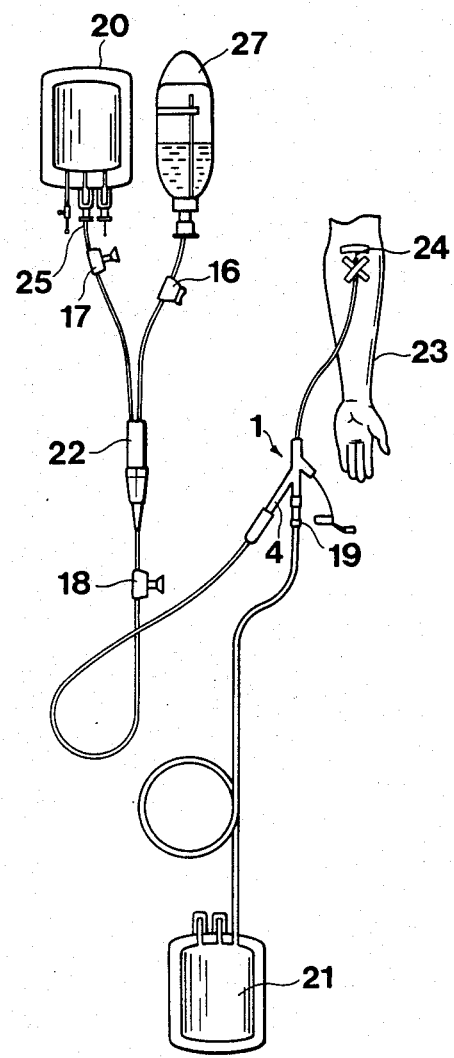

When the first blood bag 20 is filled with plenty of blood, the section of tubing to the first blood bag 20 is sealed with a tube sealer or a pair of aluminum rings (not shown). The tubing is then severed therebetween to separate the first blood bag 20, as shown in FIG. 4b.

The first blood bag 20 is then centrifuged to separate the whole blood into plasma, platelets, and other blood cells.

While the whole blood in the first blood bag 20 is being processed, a flow of saline is introduced into the donor's arm from the saline bottle 27 through the Y set 22, the branch tube 1, and the venipuncture needle 24 to maintain the patency of the needle 24.

The red cell concentrate and the plasma thus separated are independently returned to the donor 23 by connecting an outlet port 25 of the first blood bag 20 to the second inlet line of the Y set 22 having the clamp 17 thereon, and through the Y set 22, branch tube 1 and the venipuncture needle 24. In the meantime, the platelet concentrate is transfused to another patient.

When the return transfusion is completed, the frangible valve 19 is broken to open a flow path toward the second blood bag 21. The blood is drawn into the second blood bag 21 through the venipuncture needle 24 which is already punctured into the donor's arm. The blood collected in the second blood bag 21 is processed and returned in a similar manner as the first blood bag 20.

The tube assembly of the present invention has the following benefits.

Since the open end 6 extends beyond the cut edge 26, of the plug member 2 after tearing off the plug member 2 at the thin-walled portion 15, the end 6 can be directly observed to ensure safer connection to the exposed end 6 of another member such as a spiked end or a connector of a tubing. It is then possible to avoid the contamination of the flow path by an inadvertent contact of another member with the outer wall of the plug residue.

Since the plug member 2 is fixedly secured to the tubular body at the first inner-wall portion 9 on the proximal side of the thin-walled portion 15 and the space 3 is defined within the second inner-wall portion 10, it is easy to tear off the plug member 2 at the thin-walled portion 15 even when the plug member 2 is made of a relatively flexible material.

We claim:

1. A tube assembly with a breakaway plug of a relatively rigid material comprising:
  a tubular body having at least two open ends at least one of said ends having an end surface and an outer surface portion; and
  a plug member having an open end and a closed end, said plug member being mounted on said one open end of said tubular body,
  said plug member including on its inner surface;
    an inner closing surface closing off said closed end,
    a first inner-wall portion extending from the open end toward the closed end a predetermined distance, said first inner-wall portion being fixedly secured to said one open end of said tubular body, and
    a second inner-wall portion extending from the first inner-wall portion to the closed end to define a space between the plug member and the tubular body, said space including two portions:
    a first space portion extending circumferentially between the second inner-wall portion of said plug member and the outer surface portion of the open end of said tubular body, and a second space portion extending between said inner closing surface of the plug member and the end surface of the open end of said tubular body, said plug member including on its outer surface a thin-walled frangible portion, which is breakable to allow separation of said plug member from said tubular body, said thin-walled frangible portion being located on the outer surface of said second inner-wall portion and located radially outside said first space portion, said one open end of the tubular body extending in said space beyond the thin-walled frangible portion toward the closed end of the plug member.

2. The tube assembly of claim 1 wherein said second inner wall portion has a relatively layer inner diameter then the first inner wall portion.

3. The tube assembly of claim 1 wherein said one open end of the tubular body includes on its outer surface a first outer-wall portion on which the first inner-wall portion of the plug member is fixedly secured, and a second outer-wall portion defining the first space portion, said second outer-wall portion having a relatively smaller outer diameter than said first-outer wall portion.

* * * * *